United States Patent [19]

Sherwin

[11] Patent Number: 4,640,290

[45] Date of Patent: Feb. 3, 1987

[54] SHIELDED, SELF-PREPARING ELECTRODE SUITABLE FOR ELECTROENCEPHALOGRAPHIC MAPPING

[75] Inventor: Gary W. Sherwin, South Huntingdon Township, Westmoreland County, Pa.

[73] Assignee: Westinghouse Electric Corp., Pittsburgh, Pa.

[21] Appl. No.: 727,058

[22] Filed: Apr. 25, 1985

[51] Int. Cl.⁴ .............................................. A61B 5/04
[52] U.S. Cl. ..................................... 128/642; 128/644
[58] Field of Search .............................. 128/639–644, 128/731

[56] References Cited

U.S. PATENT DOCUMENTS

| | | | |
|---|---|---|---|
| 3,505,993 | 4/1970 | Lewes et al. | 128/643 |
| 3,580,242 | 5/1971 | La Croix | 128/642 |
| 3,620,208 | 11/1971 | Higley et al. | 128/639 |
| 3,841,310 | 10/1974 | Goldstein | 128/642 |
| 4,004,578 | 1/1977 | Palmius | 128/642 X |
| 4,350,164 | 9/1982 | Allain, Jr. | 128/639 |

FOREIGN PATENT DOCUMENTS 2555281 6/1977 Fed. Rep. of Germany ...... 128/639

*Primary Examiner*—Lee S. Cohen
*Attorney, Agent, or Firm*—Daniel C. Abeles

[57] ABSTRACT

A self-preparing electrode, suitable for EEG mapping, includes a metallic cylinder separated by a dielectric cylinder from a socket for a probe assembly. The probe assembly is preferably a tulip probe removably held by the socket which is connectable to an inner conductor of a coaxial cable. The metallic cylinder includes a cavity into which the tip of the tulip probe is partially depressed when the probe assembly and shell are placed on the skin of a patient. The tip of the tulip probe has multiple points which penetrate the dead skin layer and make electrical contact with the blood-rich skin layer of the patient. The electrode is held in place by straps attached to the shell of the electrode.

17 Claims, 7 Drawing Figures

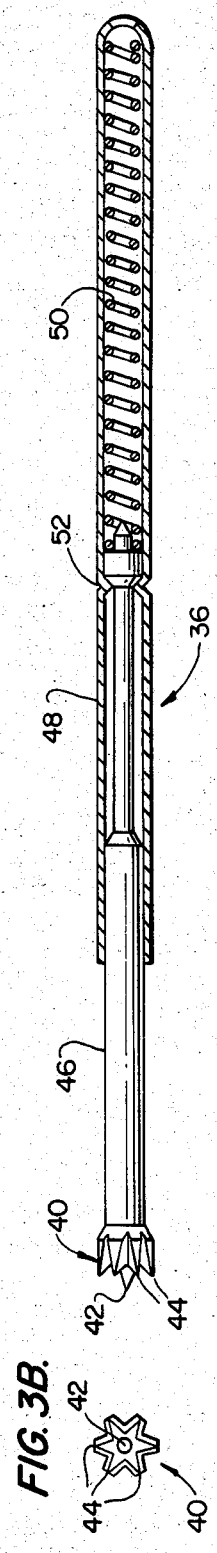
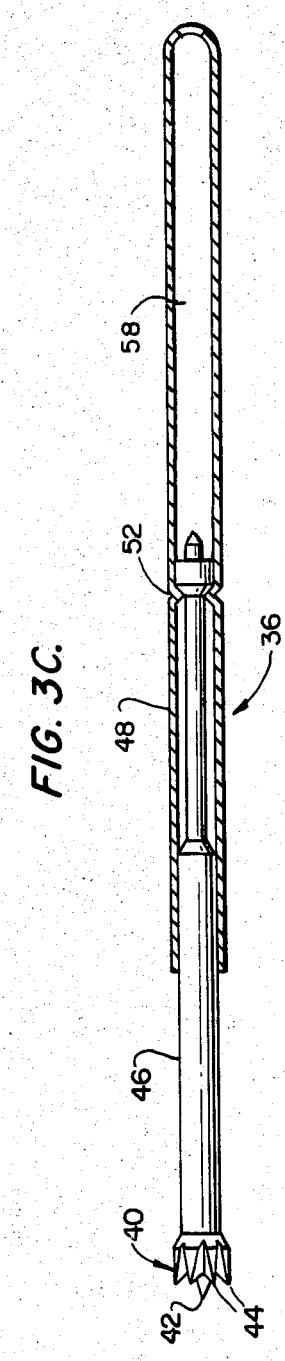
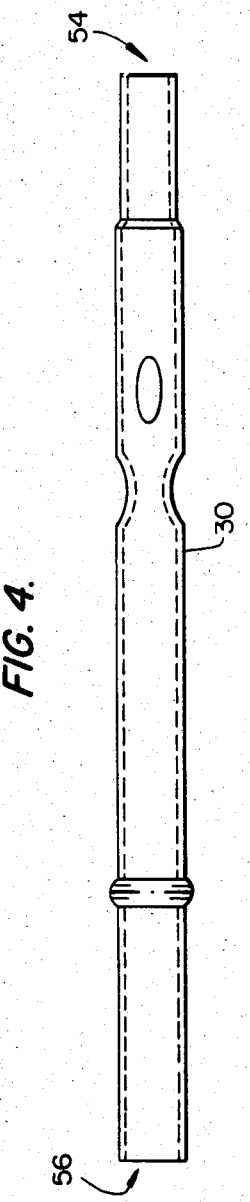

SHIELDED, SELF-PREPARING ELECTRODE SUITABLE FOR ELECTROENCEPHALOGRAPHIC MAPPING

CROSS REFERENCE TO RELATED APPLICATIONS

This application is related to the following concurrently filed copending U.S. patent applications, all assigned to the assignee of the present invention: Electroencephalographic (EEG) Cap by Sherwin having U.S. Ser. No. 727,031; Evoked Potential Autorefractometry System by Bernard, Roth, Mohan, Sherwin and Zomp having U.S. Ser. No. 727,032; Low Noise EEG Probe Wiring System by Sherwin having U.S. Ser. No. 727,060; and Narrow Band EEG Amplifier by Sherwin and Zomp having U.S. Ser. No. 727,056.

BACKGROUND OF THE INVENTION

1. Field of the Invention

The present invention relates in general to a an electroencephalographic electrode or probe used for sensing the potential of skin and in particular to a self-preparing electrode or probe which is easily and securely held in place with little preparation of the patient, thus facilitating electroencephalographic mapping.

2. Description of the Related Art

Electroencephalograms and electrocardiograms are commonly performed on medical patients by sensing the potential of skin covering the brain and heart, respectively. An electroencephalogram (hereinafter EEG), is prepared by placing one or more electrodes in electrical contact with the blood-rich epidermis layer of skin on the scalp and connecting a reference lead, for example, to an ear lobe. The electrode(s) and refrence lead are connected to an amplifier and other equipment which use the signals sensed by the electrodes to prepare the EEG.

A conventional EEG electrode, Part No. H304075 manufactured by Beckman, is illustrated in FIGS. 1A and 1B. The surface of the conventional EEG electrode which makes contact with the scalp is illustrated in FIG. 1A. To make contact with blood-rich epidermis layer of the skin, a portion of the scalp is shaved to remove hair and dead skin or keratinous layer is scraped or abraded away at the point at which the electrode is to be attached. An adhesive is placed on the outer circular surface 10 and an electrolyte cream or gel is placed in the center 12. As indicated by the cross-section of the conventional EEG electrode, illustrated in FIG. 1B, the center 12 is indented or set back from the surface 10. A silver plug 14 is surrounded by a plastic cover 16 on three sides and is exposed only on the surface 12 where the electrolyte gel is applied. A wire 18 is connected to the silver plug 14 for making connections to an electroencephalograph.

While the conventional EEG electrode is satisfactory for many applications, it has several drawbacks, especially when used for EEG mapping in which electrodes are attached at many points on a scalp. Since the conventional electrode requires shaving of the area to which the electrode is attached and removal of dead skin, large areas of a patient's head must be shaved and the patient experiences the discomfort of the abrasion process during EEG mapping using the conventional electrode. In addition, conventional electrodes can be inadvertently released from a patient's head due to movement or deterioration of the adhesive and the adhesive must be removed between applications in order to ensure proper contact. Finally, no shielding is provided for the electrode or wire with the result that electromagnetic waves of many frequencies, such as 60 Hz must be eliminated from the signal produced by the EEG electrode via the electroencephalograph or an amplifier used in conjunction therewith.

SUMMARY OF THE INVENTION

An object of the present invention is to provide a shielded electrode to reduce electromagnetic interference during electroencephalography or electrocardiography.

Another object of the present invention is to provide a shielded electrode which does not require adhesive.

A further object of the present invention is to provide a shielded electrode which is capable of precise positioning.

Another object of the present invention is to provide a shielded electrode which does not require any preparation of a patient.

A further object of the present invention is to provide a shielded electrode which can be closely packed in an array for electroencephalographic mapping.

An additional object of the present invention is to provide a self-preparing electrode that can be mounted in EEG cap used in an evoked potential auto-refractometry system.

The above objects are attained by providing a shielded self-preparing electrode comprising a potential sensing device, connectable to the inner conductor of a coaxial cable, for penetrating a dead skin layer and sensing the electrical potential of a blood-rich skin layer and a shell, connectable to the outer conductor of the coaxial cable, for securely holding and providing electromagnetic shielding for the potential sensing device.

These objects, together with other objects and advantages which will be subsequently apparent reside in the details of construction and operation as more fully hereinafter described and claimed, reference being had to the accompanying drawings forming a part hereof, wherein like reference numerals refer to like parts throughout.

BRIEF DESCRIPTION OF THE DRAWINGS

FIG. 3A is a partial cross sectional view of the probe assembly 36 used in the shielded electrode illustrated in FIG. 2;

FIG. 3B is a front view of the tip 40 of the probe assembly 36 in FIG. 3A; FIG. 3C is a partial cross-sectional view of a gas filled probe assembly 36; and FIG. 4 is a side view of the socket 30 illustrated in FIG. 2.

DESCRIPTION OF THE PREFERRED EMBODIMENTS

Figure 1A:
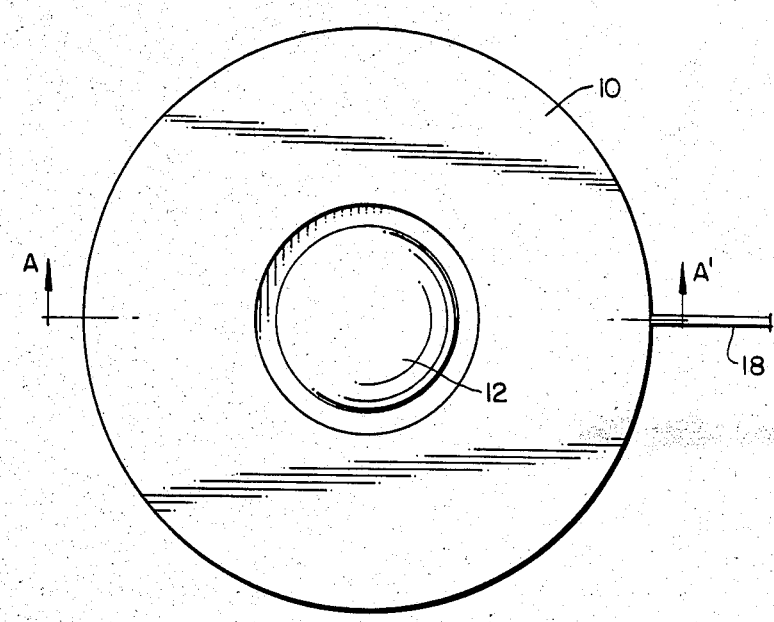
FIG. 1A is a top view of a conventional EEG electrode, viewed from the surface applied to the scalp of a patient.
Figure 1B:
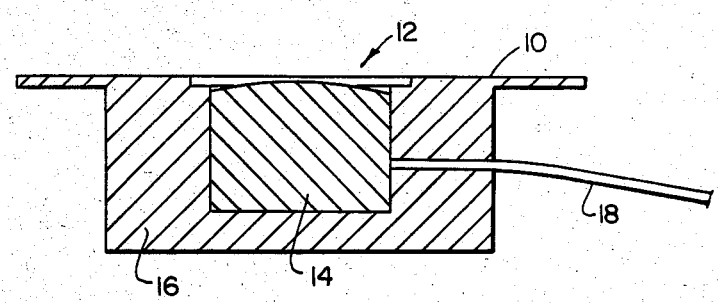
FIG. 1B is a cross-sectional diagram, taken along the line A-A' in FIG. 1A, of the conventional EEG electrode.
Figure 2:
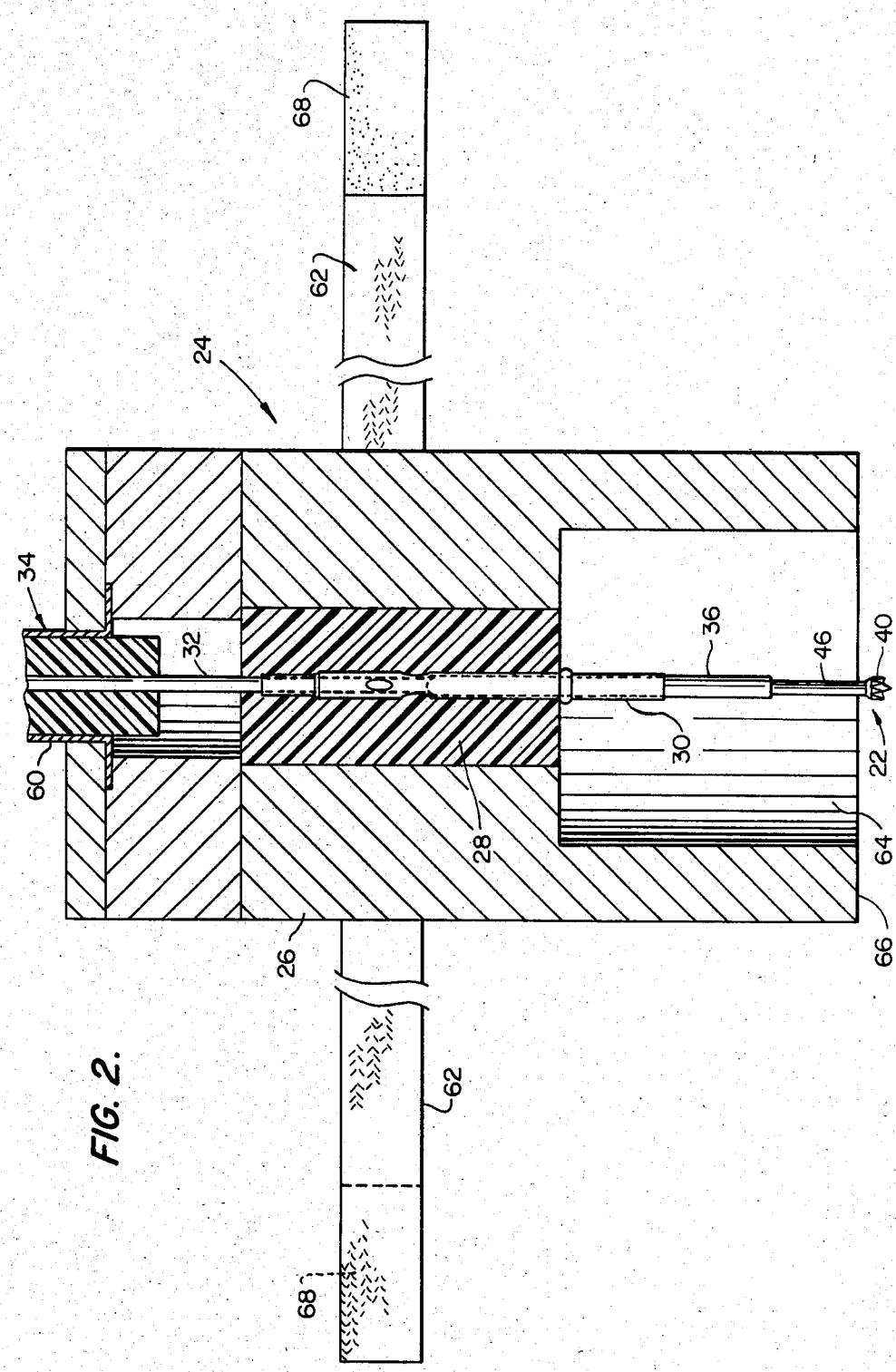
FIG. 2 is a cross-sectional view of a shielded self-preparing electrode according to the present invention.

A shielded self-preparing electrode according to the present invention is illustrated in cross-section in FIG. 2. A potential sensing device 22 is located in the center of a shell 24 which provides electromagnetic shielding. The shell is formed from a metallic cylinder or socket holder 26 which is separated from the potential sensing device by a dielectric 28. The metallic cylinder 26 may easily be formed by machining a block of aluminum or forming a tube of aluminum or copper. The dielectric 28 may be made of many materials, one example is LEXAN, formed in a cylinder which can be fixed in the aluminum cylinder 26. Another example is heat shrink tubing, as illustrated in FIG. 4 of the co-pending application having Ser. No. 727,031, which is incorporated herein by reference.

The potential sensing device is preferably made from two components, the first being a socket 30 which can be soldered to the inner conductor 32 of a coaxial cable 34 and the second being a probe assembly 36 being removably held by the socket 30. The probe assembly 36 is preferably a gold-plated tulip probe manufactured by Ostby and Barton Company under part no. 100817-S which is illustrated in FIGS. 3A and 3B. Ostby and Barton Co. also manufactures a suitable socket 30, part no. 60004, which holds the tulip probe 36 and is illustrated in FIG. 4.

The tulip probe 36 is commonly used as a probe by the semiconductor industry, but includes features which make it highly suitable for use in an EEG electrode. As illustrated in FIGS. 3A and 3B, the tulip probe 36 includes a tip 40 with a center point 42 surrounded by six wedge shaped outer points 44. This structure is capable of piercing the dead skin layer and making contact with the blood-rich skin layer underneath without causing bleeding because the pressure against the skin is dispersed due to the multiple points 42 and 44 and the wedge shape of the points. The wedge shape of each point, as illustrated in FIGS. 3A and 3B, has a pressure dispersing surface that is substantially diagonal with respect to the penetrating face of the tip 40. The pressure dispersing face increases in width as the surface moves toward the center of the tip thereby providing a controlled increase in the area of the pressure dispersing surface, so that penetration of the blood-rich skin layer is prevented.

In addition, the wedge shape of the multiple points 42 and 44 provides self-cleaning properties making the tulip probe 36 very suitable for multiple applications without cleaning between applications.

The tip 40 is attached to a piston 46 which is partially encircled by a body 48. A spring 50 forces the piston 46 against a roll crimp 52 so that the piston 46 is resistantly slidable within the body 48 allowing excessive force to be absorbed by the spring 50. The overall length of part no. 100817-S is approximately one and one-third inches and the tip 40 has a maximum diameter of approximately one-twentieth of an inch. The spring 50 provides approximately two and one-half to six ounces of pressure so that the tip 40 can penetrate the dead skin layer without puncturing the blood-rich skin layer and causing bleeding. The socket 30 is attached to the inner conductor 32 at a first end 54 and securely holds the tulip probe 36 at a second end 56. However, if the tulip probe 36 is damaged, or the spring becomes worn, the tulip probe 36 may be removed from the socket 30 and replaced.

Alternatively, pressure against the roll crimp 52 may be supplied by other means. For example, a compressed gas 58 may be used in place of the spring 50 as illustrated in FIG. 3C. The probe assembly 36 would then have to be sealed to provide containment of the gas.

The shell 24 can be attached to the outer conductor 60 of the coaxial cable 34 (FIG. 2) and to straps 62 by which the electrode can be attached to the body of a patient. The shell 24 also includes a cavity 64 into which the tip 40 can be depressed by the skin of the patient. The socket 30 and tulip probe 36 are mounted in the shell 24 so that the tip 40 normally extends beyond the edge of the shell 24 as illustrated in FIG. 2. When the end 66 of the cylinder 26 is pressed against the scalp of a patient, the tip 40 is pushed partially into the cavity 64 as the tip 40 penetrates the dead skin layer to the blood-rich skin layer of the patient while the end 66 of the cylinder 26 prevents the application of additional force to the tip 40.

The straps 62 can be attached in many ways to the shell 24 of the probe for attaching the probe to the body of the patient. The straps 62 may be a single continuous elastic band or two or more straps. If two straps are used, some type of coupling means such as hook and loop (Velcro) patches 68 are preferably used. It is also possible to mount one or more shielded probes according to the present invention in a relatively rigid plastic strap for a helmet which fits on a patient's head. An example of such a plastic strap can be found in a hard hat or chemical shield and the metal shell 24 would have a roll crimp on the outside which would allow the shell 24 to be snapped into a hole in the plastic band. A large number of shielded electrodes may also be attched to a dome-type helmet in a closely packed array to perform EEG mapping.

The skin piercing features of the tip 40 eliminate the need for skin abrasion and shaving of the patient prior to attaching the electrode. When an electrode according the present invention is used with a conventional amplifier, a resistance test should be performed to meet the input impedance requirements of the amplifier, typically 5 kilohms. If the resistance exceeds the minimum impedance requirement, a slight abrasion of the skin by moving the probe slightly over the area to be sensed is sufficient; however, the normal process of attaching the straps or helmet is usually sufficient.

When used with a low noise EEG probe wiring system and a sensitive narrow band EEG amplifier, such as those described in the copending applications, no electrolyte gel or solution is required. When used with conventional amplifiers, a drop of electrolyte is all that is required prior to performing an EEG on a patient. Of course the application of an electrolyte after the probe is in position on the patients scalp will further enhance conductance even when used with the low noise wiring system and the narrow band amplifier.

This probe, because of its self-preparing, self-cleaning and low noise characteristics is particularly suitable for use in an evoked potential autorefractometry system for prescribing eyeglass lenses in an optometrist's office where a series of patients would have the electrode fixed against their scalp.

The many features and advantages of the present invention are apparent from the detailed specification, and thus it is intended by the appended claims to cover all such features and advantages of the probe which fall within the true spirit and scope of the invention. Further, since numerous modifications and changes will readily occur to those skilled in the art, it is not desired to limit the invention to the exact construction and operation illustrated and described. Accordingly, all suitable modifications and equivalents may be resorted to, falling within the scope and spirit of the invention.

What is claimed is:

1. A shielded, self-preparing electrode, connectable to a coaxial cable having inner and outer conductors, for sensing an electrical potential of a blood-rich skin layer covered by a dead skin layer, said electrode comprising:
   potential sensing means, connectable to the inner conductor of the coaxial cable, for penetrating the dead skin layer, sensing the electrical potential of the blood-rich skin layer, absorbing a part of a penetrating force exceeding a force required to penetrate the dead layer of skin and helping prevent penetration of the blood-rich skin layer; and
   shell means, connectable to the outer conductor of said coaxial cable, for securely holding and providing electromagnetic shielding for said potential sensing means and absorbing a remainder of the penetrating force exceeding the force required to penetrate the dead layer of skin.

2. An electrode as recited in claim 1,
   wherein said potential sensing means comprises:
   a probe having a tip including wedge shaped points and;
   a spring coupled to said probe and absorbing the part of the excess force, and
   said shell means comprises a cylinder coupled to said spring, surrounding said probe and spring, and which contacts the skin when said spring is compressed beyond a predetermined point and prevents further probe movement.

3. A shielded, self-preparing electrode, connectable to a coaxial cable having inner and outer conductors, for sensing an electrical potential of a blood-rich skin layer covered by a dead skin layer, said electrode comprising:
   potential sensing means, connectable to the inner conductor of the coaxial cable, for penetrating the dead skin layer and sensing the electrical potential of the blood-rich skin layer, said potential sensing means comprising:
   dead skin piercing means for piercing the dead skin layer to make electrical contact with the blood-rich skin layer; and
   socket means, having first and second ends, connectable to the inner conductor of the coaxial cable at the first end, for removably holding said dead skin piercing means at the second end, and
   shell means, connectable to the outer conductor of said coaxial cable, for securely holding and providing electromagnetic shielding for said potential sensing means.

4. An electrode as recited in claim 3,
   wherein said dead skin piercing means comprises:
   skin contact means for making electrical contact with the blood-rich skin layer without causing bleeding; and
   pressure means for forcing said skin contact means toward the blood-rich skin layer to maintain electrical contact with the blood-rich skin layer without causing bleeding, when said shell means and said skin contact means are both in contact with the dead skin layer, and
   wherein said electrode further comprises body attachment means for holding said shell means and said skin contact means in contact with the dead skin layer.

5. An electrode as recited in claim 4,
   wherein said shell means has a cavity surrounding said skin contact means,
   wherein said pressure means normally forces said skin contact means to project beyond said shell means, and
   wherein said skin contact means is resistantly slidable into the cavity.

6. An electrode as recited in claim 4, wherein said body attachment means comprises an elastic band attached to said shell means.

7. An electrode as recited in claim 4, wherein said body attachment means comprises:
   at least two straps attached to said shell means; and
   coupling means attached to at least one of said straps.

8. An electrode as recited in claim 7, wherein said coupling means comprises hook and loop patches attached to said straps.

9. An electrode as recited in claim 3,
   wherein said shell means has a cavity surrounding said dead skin piercing means, and
   wherein said dead skin piercing means comprises:
   skin contact means for penetrating the dead skin layer without causing bleeding, said skin contact means being resistantly slidable into the cavity of said shell means; and
   pressure means for forcing said skin contact means to normally project beyond said shell means and to maintain electrical contact with the blood-rich skin layer without causing bleeding when said shell means and said skin contact means are both in contact with the dead skin layer.

10. An electrode as recited in claim 9, wherein said shell means comprises:
    a metallic cylinder, connectable to the outer conductor of said coaxial cable, having the cavity at one end; and
    a dielectric disposed between said socket means and said metallic cylinder.

11. An electrode as recited in claim 10, further comprising body attachment means for holding said metallic cylinder and said skin contact means in contact with the dead skin layer.

12. An electrode as recited in claim 9, wherein said pressure means comprises a spring coupled to said skin contact means.

13. An electrode as recited in claim 9, wherein said pressure means comprises:
    a compressed gas; and
    containment means for enclosing said compressed gas and for exerting pressure on said skin contact means.

14. An electrode as recited in claim 9, wherein said skin contact means comprises a self cleaning tip.

15. A shielded, self-preparing electrode, connectable to a coaxial cable having inner and outer conductors, for sensing an electrical potential of a blood-rich skin layer covered by a dead skin layer, said electrode comprising:
    a probe assembly, comprising:
    a piston having a multiple-point tip for piercing the dead skin layer to make electrical contact with the blood-rich skin layer;
    a spring, abutting said piston, for forcing the multiple-point tip toward the blood-rich skin layer to maintain electrical contact with the blood-rich skin layer without causing bleeding; and
    a body holding said piston and said spring;

a socket, having a first end connectable to the inner conductor of the coaxial cable and a second end removably holding said probe assembly;

a shell, having a cavity and an insulator, connectable to the outer conductor of said coaxial cable, securely holding said socket in contact with the insulator and providing electromagnetic shielding for said probe assembly, the multiple-point tip of said piston being resistantly slidable into the cavity of said shell; and body attachment means for holding said shell and the multiple-point tip of said piston in contact with the dead skin layer.

16. An electrode as recited in claim 15, wherein said shell comprises:

a metallic cylinder, connectable to the outer conductor of the coaxial cable, having the cavity at one end; and a dielectric insulator cylinder disposed between said socket and said metallic cylinder.

17. An electrode as recited in claim 16, wherein said dielectric cylinder is formed of LEXAN.

* * * * *